US012336821B2

(12) United States Patent
Taulu et al.

(10) Patent No.: US 12,336,821 B2
(45) Date of Patent: Jun. 24, 2025

(54) APPARATUSES, SYSTEMS, AND METHODS FOR SUPPRESSION OF ARTIFACTS IN NON-INVASIVE ELECTROMAGNETIC RECORDINGS

(71) Applicant: University of Washington, Seattle, WA (US)

(72) Inventors: Samu Taulu, Seattle, WA (US); Eric Larson, Seattle, WA (US)

(73) Assignee: University of Washington, Seattle, WA (US)

( * ) Notice: Subject to any disclaimer, the term of this patent is extended or adjusted under 35 U.S.C. 154(b) by 840 days.

(21) Appl. No.: 17/271,153

(22) PCT Filed: Aug. 22, 2019

(86) PCT No.: PCT/US2019/047755
§ 371 (c)(1),
(2) Date: Feb. 24, 2021

(87) PCT Pub. No.: WO2020/041621
PCT Pub. Date: Feb. 27, 2020

(65) Prior Publication Data
US 2021/0186400 A1 Jun. 24, 2021

Related U.S. Application Data

(60) Provisional application No. 62/722,341, filed on Aug. 24, 2018.

(51) Int. Cl.
*A61B 5/246* (2021.01)
*A61B 5/00* (2006.01)
*A61B 5/377* (2021.01)

(52) U.S. Cl.
CPC .............. *A61B 5/246* (2021.01); *A61B 5/377* (2021.01); *A61B 5/4064* (2013.01); *A61B 5/7203* (2013.01); *A61B 5/7235* (2013.01)

(58) Field of Classification Search
CPC ....... A61B 5/246; A61B 5/377; A61B 5/4064; A61B 5/7203; A61B 5/7235
See application file for complete search history.

(56) References Cited

U.S. PATENT DOCUMENTS 4,736,751 A * 4/1988 Gevins .................. A61B 5/372
600/545
5,417,211 A * 5/1995 Abraham-Fuchs .... G16H 50/20
706/924

(Continued)

FOREIGN PATENT DOCUMENTS

JP 2008161637 A 7/2008
JP 2011067497 A 4/2011

(Continued)

OTHER PUBLICATIONS

Gramfort, Alexandre et al., "MNE software for processing MEG and EEG data", NeuroImage 86, Oct. 24, 2013, pp. 446-460.

(Continued)

*Primary Examiner* — Dixomara Vargas
(74) *Attorney, Agent, or Firm* — Dorsey & Whitney LLP (57) ABSTRACT

Embodiments disclosed herein directed to systems, apparatuses, and methods for the suppression of artifacts in non-invasive electromagnetic recordings. A data set, such as an electroencephalography (EEG) or magnetoencephalography (MEG) data set may be recorded by a number of sensors. The data set may include contributions from a signal of interest and from artifacts. The contribution of artifacts may be suppressed by splitting the data set into projected data and residual data based on a spatial model of the signal of interest. The projected data may contain contributions from the signal of interest and artifacts, while the residual data may primarily contain contributions from artifacts. The (Continued)

projected and residual data may be compared to remove or reduce the contribution of artifacts from the projected data.

20 Claims, 7 Drawing Sheets

(56) References Cited

U.S. PATENT DOCUMENTS

| | | | | |
|---|---|---|---|---|
| 6,144,872 | A * | 11/2000 | Graetz | A61B 5/372 |
| | | | | 600/407 |
| 9,089,310 | B2 | 7/2015 | Isenhart et al. | |
| 9,116,835 | B1 * | 8/2015 | Smyth | A61B 5/369 |
| 9,642,554 | B2 | 5/2017 | Simola et al. | |
| 10,307,105 | B2 | 6/2019 | Taulu et al. | |
| 10,531,805 | B2 * | 1/2020 | Bickford | A61B 5/375 |
| 10,799,134 | B2 * | 10/2020 | Sitt | A61B 5/245 |
| 10,859,620 | B2 * | 12/2020 | Bickford | G01R 29/12 |
| 2003/0093004 | A1 * | 5/2003 | Sosa | A61B 5/24 |
| | | | | 600/544 |
| 2005/0286190 | A1 | 12/2005 | Rostron et al. | |
| 2006/0149160 | A1 | 7/2006 | Kofol et al. | |
| 2007/0106170 | A1 * | 5/2007 | Dunseath | A61B 5/291 |
| | | | | 600/383 |
| 2008/0312523 | A1 * | 12/2008 | Dunseath | H03F 3/26 |
| | | | | 600/383 |
| 2009/0099473 | A1 * | 4/2009 | Dunseath | A61B 5/6814 |
| | | | | 600/383 |
| 2012/0245653 | A1 * | 9/2012 | Bikson | G16H 50/50 |
| | | | | 607/45 |
| 2013/0317337 | A1 * | 11/2013 | Wu | A61B 5/243 |
| | | | | 600/409 |
| 2013/0324832 | A1 * | 12/2013 | Wu | A61B 5/242 |
| | | | | 600/409 |
| 2014/0148723 | A1 | 5/2014 | Nierenberg et al. | |
| 2014/0316230 | A1 * | 10/2014 | Denison | A61B 5/168 |
| | | | | 600/545 |
| 2014/0343882 | A1 | 11/2014 | Taulu et al. | |
| 2016/0113587 | A1 * | 4/2016 | Kothe | A61B 5/7214 |
| | | | | 600/559 |
| 2016/0143541 | A1 * | 5/2016 | He | A61B 5/374 |
| | | | | 600/407 |
| 2016/0157742 | A1 * | 6/2016 | Huang | A61B 5/7235 |
| | | | | 600/409 |
| 2017/0113046 | A1 | 4/2017 | Fried et al. | |
| 2017/0332933 | A1 * | 11/2017 | Krishnaswamy | A61B 5/336 |
| 2018/0236230 | A1 * | 8/2018 | Pilly | A61B 5/24 |
| 2019/0201691 | A1 * | 7/2019 | Poltorak | A61B 5/165 |
| 2019/0247662 | A1 * | 8/2019 | Poltroak | A61N 1/36025 |
| 2020/0222008 | A1 * | 7/2020 | Jensen | A61B 5/374 |

FOREIGN PATENT DOCUMENTS

| | | |
|---|---|---|
| JP | 2018023586 A | 2/2018 |
| WO | 2004081595 A1 | 9/2004 |
| WO | 2012004458 A1 | 1/2012 |
| WO | 2017205734 A1 | 11/2017 |

OTHER PUBLICATIONS

Jas, Mainak et al., "MEG/EEG group study with MNE: recommendations, quality assessments and best practices", https://www.biorxiv.org/content/10.1101/240044v1.full; bioRXiv, Dec. 18, 2017, pp. 1-30.

Larson, Eric et al., "Reducing Sensor Noise in MEG and EEG Recordings Using Oversampled Temporal Projection", IEEE Transactions on Biomedical Engineering, vol. 65, No. 5, Apr. 19, 2018, pp. 1002-1013.

Mutanen, Tuomas P et al., "Automatic and robust noise suppression in EEG and MEG: The SOUND algorithm", Neuroimage 166, Feb. 1, 2018, 135-151.

Taulu, Samu et al., "Applications of the Signal Space Separation Method", IEEE Transactions on Signal Processing, vol. 53, No. 9, Sep. 2005, pp. 3359-3372.

Taulu, Samu et al., "Presentation of electromagnetic multichannel data: The signal space separation method", Journal of Applied Physics 97, 124905, Jun. 21, 2005, pp. 1-10.

Taulu, Samu et al., "Spatiotemporal signal space separation method for rejecting nearby interference in MEG measurements", Physics in Medicine & Biology, 51, Institute of Physics Publishing, Mar. 16, 2006, pp. 1759-1768.

Uusitalo, Mikko A. et al., "Signal-space projection method for separating MEG or EEG into components", Medical & Biological Engineering & Computing 35, Apr. 1997, pp. 135-140.

EESR dated Apr. 13, 2022 for EP Application No. 19852360.7.

Gramfort, Alexandre, et al., "MNE Software for Processing MEG and EEG Data", NeuroImage, vol. 86, Oct. 2013, 15 pages.

Taulu, Samu, et al., "Removal of Magnetoencephalographic Artifacts With Temporal Signal-Space Separation: Demonstration With Single-Trial Auditory-Evoked Responses", Human Brain Mapping, vol. 30, No. 5, May 2009, 11 pages.

International Search Report and Written Opinion for Application No. PCT/US2019/047755, dated Dec. 19, 2019.

Grouiller, et al., "A Comparative Study of Different Artefact Removal Algorithms for EEG Signals Acquired During Functional MRI", Neuroimage vol. 38, Issue 1, Oct. 15, 2007, pp. 124-137.

Niazy, et al., "Removal of FMRI Environment Artifacts From EEG Data Using Optimal Basis Sets", Neuroimage vol. 28, Sep. 2005, pp. 720-737.

Sekihara, Kensuke et al., Subspace-Based Interference Removal Methods for a Multichannel Biomagnetic Sensor Array, Journal of Neural Engineering, Aug. 18, 2017, 21 pages.

* cited by examiner

APPARATUSES, SYSTEMS, AND METHODS FOR SUPPRESSION OF ARTIFACTS IN NON-INVASIVE ELECTROMAGNETIC RECORDINGS

CROSS-REFERENCE TO RELATED APPLICATION(S)

This application is a 35 U.S.C. § 371 National Stage Application of PCT Application No. PCT/US2019/047755, filed on Aug. 22, 2019, which claims the benefit of U.S. Provisional Application No. 62/722,341, filed Aug. 24, 2018, the entire contents of which are hereby incorporated by reference herein.

BACKGROUND

Various processes in the body produce electromagnetic signals. For example, the depolarization of a neuron or group of neurons produces an electrical current, which in turn may generate electrical and magnetic fields. Measuring these fields may be useful for non-invasive monitoring of activity in the body.

For example, non-invasive analysis of electric phenomena inside a conductor, such as the human brain, may be performed by measuring the corresponding electromagnetic field (EMF) distribution at multiple locations that are close to the conductor but outside of it (e.g., by placing sensors on or outside of the skull). Such measurements may allow analysts to make inferences about the underlying neural current distribution and its neuroscientific or clinical significance. The techniques of measuring the electric voltage or the magnetic field distribution outside the head may generally be referred to as electroencephalography (EEG) and magnetoencephalography (MEG), respectively. In both techniques, one of the main challenges is that the brain signals are relatively weak compared to the EMF contributions arising in the environment, which are often several orders of magnitude larger.

SUMMARY

In at least one aspect, the present disclosure relates to a method. The method includes positioning a plurality of sensors outside a conductor. A current inside the conductor generates an electromagnetic field. The method includes measuring a data set including a plurality of channels each measured by one of the plurality of sensors based on the electromagnetic field at the position of the sensor. The method includes generating an estimated distribution of the electromagnetic field at the positions of the plurality of sensors based on a spatial model of the electromagnetic field. The method includes separating the measured data set into a projected data set and a residual data set based on the estimated distribution of the electromagnetic field. The method includes generating a processed data set by removing artifacts from the data set or the projected data set based on a comparison of the data set or the projected data set and the residual data set to identify artifact waveforms matched between the data set or the projected data set and the residual data set.

The method may also include decomposing the data set into a plurality of waveforms including signal of interest waveforms and artifact waveforms, decomposing the residual data set into a plurality of waveforms including artifact waveforms, and comparing the plurality of waveforms from the data set to the plurality of waveforms of the residual data and removing the artifacts based on the comparison. Removing the artifacts may include projecting the original recorded or projected data set based on the residual data set. Projecting the original recorded or projected data set may take place in the temporal domain.

The method may also include decomposing the projected data set into a plurality of waveforms including signal of interest waveforms and artifact waveforms, decomposing the residual data set into a plurality of waveforms including artifact waveforms, and comparing the plurality of waveforms from the projected data to the plurality of waveforms of the residual data and removing the artifacts based on the comparison.

The conductor may be a brain and the plurality of sensors may perform an electroencephalography (EEG) measurement or a magnetoencephalography (MEG) measurement. The method may also include, based on the processed data set, monitoring a subject, diagnosing the subject, determining a treatment plan for the subject, classifying a condition of the subject, or combinations thereof.

The method may also include measuring position data with a position sensor and determining the positions of the plurality of sensors based on the position data. The method may also include refining the model based on previously recorded data. The method may also include determining a number of the plurality of sensors based on a number of degrees of freedom of the spatial model. The number of the plurality of sensors may be greater than the number of degrees of freedom. Generating the estimated distribution of the electromagnetic field may include generating the spatial model of the electromagnetic field based on an arbitrary current within the conductor.

In at least one aspect, the present disclosure may relate to a sensor including a plurality of sensors positionable about a conductor, at least one processor, and at least one memory. The plurality of sensors may produce a data set based on measurements of a signal of interest generated by a current within the conductor. The data set includes contributions from the signal of interest and contributions from artifacts. The memory is encoded with executable instructions which, when executed by the at least one processor, cause the system to produce an estimated signal of interest based on a spatial model of the signal of interest and the positions of the plurality of sensors, split the data set into projected data and residual data based on the estimated signal of interest, compare the data set or the projected data and the residual data, and generate processed data by reducing the contribution of artifacts in the data set or the projected data based on the comparison.

The conductor may be a brain and the system may collect electroencephalography (EEG) measurements or magnetoencephalography (MEG) measurements. The system may also include a stimulus mechanism configured to provide a stimulus to a subject. The executable instructions may also include instructions to cause the system to record the data set before the stimulus is provided, after the stimulus is provided, while the stimulus is provided, or combinations thereof.

The executable instructions may further include instructions to cause the system to decompose the projected data into projected waveforms, decompose the residual data into residual waveforms, match the projected waveforms and the residual waveforms, and remove the matched waveforms from the projected waveforms to generate the processed data.

The executable instructions may further include instructions to cause the system to decompose the data set into data set waveforms, decompose the residual data into residual waveforms, match the data set waveforms and the residual waveforms, and remove the matched waveforms from the data set waveforms to generate the processed data.

The system may also include position sensors configured to determine the positions of the plurality of sensors. The system may be an electroencephalography (EEG) system. The executable instructions may also include instructions to cause the system to estimate a voltage at each of the positions of the plurality of sensors based on a voltage spatial model. The plurality of sensors may be positioned about a human head and the conductor may be a human brain.

In at least one aspect, the present disclosure may relate to a method which may include positioning a plurality of sensors outside a conductor. Each of the plurality of sensors may record a voltage based on an electromagnetic field generated by a current inside the conductor. The method includes measuring a data set based on the recorded voltages and determining a plurality of positions each associated with a position of one of the plurality of sensors. The method includes determining an estimated voltage at each of the plurality of positions based on a voltage spatial model of the electromagnetic field and suppressing artifacts in the data set based on the estimated voltages.

The conductor may be a brain, and the plurality of sensors may record electroencephalography (EEG) measurements. Suppressing the artifacts in the recorded voltages may include splitting the data set into a projected data set and a residual data set by projecting the data set based on the estimated voltages, matching waveforms in the data set or the projected data set to waveforms in the residual data set, and removing matched waveforms from the data set or the projected data set.

The method may include identifying the waveforms in the projected data set and the residual data set with singular value decomposition (SVD), principal component analysis (PCA) and/or independent component analysis (ICA). The method may include refining the spatial model based on a previously recorded data set.

Determining the estimated voltage may be based on the plurality of positions about the conductor and an estimated location of the current within the conductor. The conductor may be a brain of a subject, and wherein the method further comprises, based on the data set after suppressing the artifacts, monitoring the subject, diagnosing the subject, determining a treatment plan for the subject, classifying a condition of the subject, or combinations thereof. The voltage spatial model may be based on a linear superposition of electrostatic multipole moments.

DETAILED DESCRIPTION OF PREFERRED EMBODIMENTS

The following description of certain embodiments is merely exemplary in nature and is in no way intended to limit the scope of the disclosure or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the disclosure. Moreover, for the purpose of clarity, detailed descriptions of certain features will not be discussed when they would be apparent to those with skill in the art so as not to obscure the description of embodiments of the disclosure. The following detailed description is therefore not to be taken in a limiting sense, and the scope of the disclosure is defined only by the appended claims.

Non-invasive monitoring of biological electromagnetic phenomena may be useful in a variety of applications. For example, EEG and MEG may allow for monitoring of activity in the brain, which in turn may be used for a variety of research or clinical applications. Electrical and/or magnetic sensors may be placed on or around a subject's head, which may record voltage and magnetic field, respectively, as various parts of the subject's brain are activated.

However, the measurements from the sensors may also record contributions from various artifacts, such as random noise and contributions from various other sources of electromagnetic signals (e.g., wall current, other nearby equipment, electromagnetic activity in the subject other than the signals of interest, etc.). Since the signals of interest from the subject may generally be weak compared to the sources of artifact, it may generally be difficult to discern the signals of interest from the artifact in the recorded signals.

One or more types of filtering may be used to separate the signals of interest from the artifacts in the recorded signals. However, some types of conventional filtering may require knowledge (and/or one or more assumptions) about the characteristics of the artifacts' contribution to the measured signal. For example, it may require assumptions about a frequency of the artifacts. Other types of conventional filtering may separate the measured signal into different components, but may require manual identification of which components are due to a signal of interest and which are due to artifacts. It may be advantageous to filter the measured signal automatically, without the need to assume or know the characteristics of the artifacts.

The present disclosure is directed to apparatuses, systems, and methods for suppression of artifacts in non-invasive electromagnetic recordings. Signals may be recorded using a number of sensors positioned around a subject (e.g., EEG and/or MEG sensors positioned around a subject's head). The signals may be based on a current located inside a conductor such as a closed conductor (e.g., the brain) while the sensors are positioned outside of the conductor. Each sensor may contribute a channel to a data set based on the recordings of the sensor at the position of the sensor about the conductor. The recorded data set may include a contribution from signals of interest (e.g., brain signals) and a contribution from various artifacts. A spatial model of the electromagnetic field generated by the signal of interest may be used to model the contribution from the signal of interest at the positions of the various sensors. The recorded data may be split based on the spatial model to remove the contribution from the modeled brain signal from the measured signal. For example, the recorded data may be projected based on a spatial basis of the spatial model to generate projected data which includes contributions from artifacts and the signal of interest and a residual signal which primarily includes contributions from artifacts. The projected data and the residual data may be compared, for example by decomposing the data into waveforms and comparing the waveforms, and contributions in the recorded data which match contributions in the projected data may be removed.

The spatial model may include a magnetic field spatial model, which may be useful for MEG measurements, and an electric field spatial model (which may be expressed as a voltage spatial model) which may be useful for EEG measurements. The spatial model may be based on a hierarchical model of spatial frequencies. The spatial model may have an order which determines the complexity of the model and a number of channels needed in the recorded data.

The spatial models of the present disclosure may model the signals with sufficient accuracy at a relatively low order. In other words, most of the signal of interest may be modeled by the spatial model with relatively low order (e.g., relatively few degrees of freedom). This may be useful both to reduce the complexity of the calculations in the spatial model, and also because the number of sensor channels may be based on the degrees of freedom, a relatively low order may be associated with relatively few recording channels (e.g., sensors).

Figure 1:
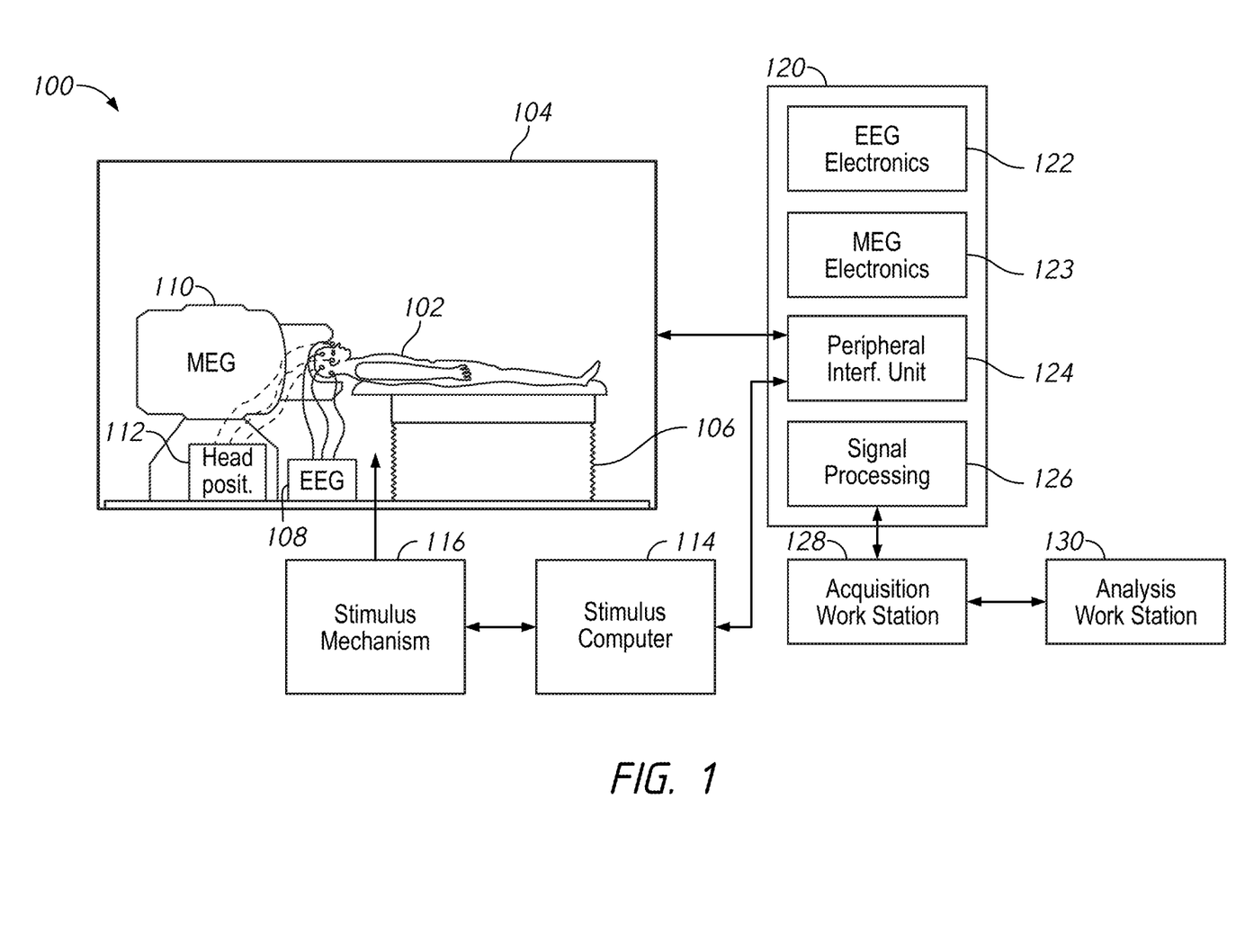
FIG. 1 is a block diagram an example environment where electromagnetic measurements may be performed.

FIG. 1 is a block diagram an example environment where electromagnetic measurements may be performed. The example environment 100 of FIG. 1 is shown set up to perform certain types of measurements on a human subject 102.

In particular the environment 100 is set up to perform MEG and EEG measurements on a subject's brain while they respond to various stimuli. Other applications may call for different configurations of the environment 100 which may be used in other example embodiments of the disclosure. Similarly, while a particular configuration of components is shown, it should be understood that various components may be separated, combined etc. For example, while separate acquisition work stations 128 and analysis work stations 130 are shown, in some embodiments they may be combined into a single work station.

The environment 100 includes a magnetically shielded room 104 which includes EEG sensors 108 and MEG sensors 110. The EEG sensors 108 and MEG sensors 110 are coupled to a subject 102. In the example embodiment of FIG. 1, the subject 102 is positioned on a support structure 106, such as a chair, bed, exam table, etc. Optional position sensors 112 may be used to track the position and orientation of the subject 102 (or a portion of the subject 102, such as the head) relative to the EEG sensors 108 and MEG sensors 110. A stimulus mechanism (e.g., a display screen, speakers, lights, etc.) may provide one or more stimuli to the subject 102 based on instructions from a stimulus computer 114. The EEG sensors 108 and MEG sensors 110 may each provide a signal which may have contributions from the subject 102 as they react (or not) to the stimuli and may also have contributions from artifacts such as noise, signal interference etc.

The signals from the EEG sensors 108 and MEG sensors 110 may be processed by one or more of the system electronics 120. The system electronics may include EEG electronics 122 to operate the EEG sensors 108, filter the raw signal from the EEG sensors 108 etc. and MEG electronics 124 which may perform similar functions for the MEG sensors 110. The system electronics 120 may include a peripheral interface unit 124 which may be used to control various aspects of the environment 100 (e.g., the stimulus computer 114, the support structure 106, etc.). The system electronics 120 may include signal processing electronics 126 which may capture the signal(s) from the EEG sensors 108 and MEG sensors 110 and may perform one or more functions on the signals such as digitization of the signals.

The system electronics 120 may be coupled to an acquisition work station 128 and analysis work station 130. The acquisition work station 128 may include acquisition software which allow a user (and/or automatically) manage the acquisition of signals from the MEG sensors 110 and EEG sensors 108 through the system electronics 120. Similarly, the analysis work station(s) 130 may allow for filtering of the data, manipulation of the data, presentation of the data, and/or review of the data either at the time the data is recorded or at a later time. The analysis work station(s) 130 may save data (e.g., locally and/or remotely) and may retrieve data from one or more previous subjects for review or analysis.

The subject 102 may be the source of electromagnetic signals of interest. In embodiments where the signals of interest are generated due to biological activity, the subject may be an organism. In the example embodiment of FIG. 1, a human subject 102 is shown, and the electromagnetic signals of interest are generated due to activity in the subject's brain. Other sources of signals of interest, such as neurons outside the brain, muscle groups, etc. may be used in other embodiments. In some embodiments the subject may be a non-human organism, such as an animal.

The subject 102 may be undergoing measurement as part of research, treatment, and/or diagnosis. In some cases the subject 102 may have, or be suspected of having, a disease which effects the electromagnetic signals of interest. For example, the subject 102 may be an epileptic, and EEG and MEG measurements of the subject's brain may be used to diagnose their epilepsy, research the nature of their epilepsy, monitor a treatment of their epilepsy etc.

The subject 102 may include a conductor in which electromagnetic activity generates a signal of interest. In some embodiments, the conductor may be a closed conductor, such as the brain. For a variety of applications it may be useful to measure electromagnetic phenomenon, such as currents, within the conductor (e.g., such as currents which may be generated by activity within the brain). It may be desirable to measure these phenomenon in a non-invasive manner, for example, in order to avoid the complications associated with placing sensors inside the brain. Accordingly, sensors 108 and 110 may be placed outside the conductor in order to measure electromagnetic fields generated within the conductor. Since the sensors 108 and 110 are positioned outside the conductor, the sensors 108 and 110 may generally be considered to be further away from a center of the conductor (or any other reference point of the conductor) than the current which generates the electromagnetic fields. This may be useful for generating the spatial model.

The EEG and/or MEG measurements may be performed while the subject 102 is in a room 104. The room 104 may be an electrically and/or magnetically shielded room, which may reduce artifacts measured by the EEG and MEG sensors 108 and 110 by mitigating interference which originates outside the room. In some embodiments the room 104 may be shielded in part to protect the MEG sensors 110 and/or EEG sensors 108 from interference which would be harmful to the electronics of the sensors.

During the EEG and/or MEG measurements, the subject 102 may be positioned on a support structure 106. The support structure 106 may help to position the subject 102 with respect to the EEG sensors 108 and/or MEG sensors 110, and may allow the subject 102 to relax, which may reduce extraneous movement of the subject 102. For example, the support structure 106 may be a chair or a bed that the subject 102 may rest upon. The support structure 106 may be adjustable and may include one or more sensors which may be used to track the position of the subject 102 relative to the EEG sensors 108 and/or MEG sensors 110.

Positioning sensors 112 may also be used to monitor the position of the subject 102 relative to the EEG sensors 108 and/or MEG sensors 110. In some embodiments, the positioning sensors 112 may measure the position of the entire subject 102. In some embodiments, the position sensors 112 may measure the position of a region of interest of the subject 102. For example, in the case of EEG and MEG measurements, the positioning sensors 112 may be head position sensors which measure the orientation and location of the subject's head relative to the sensors.

For example, in an embodiment where the MEG sensors 110 are in a structure such as a Dewar, the positioning sensors 112 may be attached to the subject's head, and each sensor may measure its distance to a matching reference location in the structure containing the MEG sensors 110. In another example, the structure containing the MEG sensors 110 may be adjustable (e.g., on a gantry) and the actuators which adjust the structure may send signals which indicate the position of the adjustable structure. The support structure 106 that the subject 102 is on may provide similar information and the positioning of the subject 102 may be determined based on the relative locations and orientations of the adjustable structure containing the MEG sensors 110 and the adjustable support structure 106.

The EEG sensors 108 may be electrodes which are positioned on or about the subject 102. Each of the EEG sensors 108 may include a resistive element (e.g., a wire) which may develop a current and/or voltage responsive to exposure to an electromagnetic field. For example, responsive to an electric field, each electrode may develop a potential (e.g., a voltage). In some embodiments, the EEG sensors 108 may be coupled by wires or wirelessly coupled to provide a measurement of the voltage of that EEG sensor. The voltages of the EEG sensors 108 may be recorded over time by the acquisition work station 128.

In some embodiments, the EEG sensors 108 may be attached to the subject 102 (e.g., attached to a subject's head) for example with an adhesive. In some embodiments, the EEG sensors 108 may be attached to a support which may then be position on the subject 102. For example, the EEG sensors 108 may be attached to a wearable such as a hat, a headband, a net, etc. which may be positioned on the subject's head.

The MEG sensors 110 may measure a magnetic field at the location of the magnetic sensor 110. For example, each of the MEG sensors 110 may be superconducting quantum interference devices (SQUIDs) which may include superconducting elements which produce a signal proportional to the magnetic field at the SQUID. The MEG sensors 110 may measure a vector of the magnetic field. In some embodiments, the MEG sensors 110 may be positioned in an insulating structure, such as a Dewar. The Dewar may be shaped to be positioned around the subject 102 (e.g., around the subject's head) such that the MEG sensors 110 are close to the subject 102, but the subject 102 is protected from the cryogenic temperatures of the MEG sensors 110.

The EEG and MEG sensors 108 and 110 may provide a data set such as a matrix of data. The data set may include a number of 'channels' each of which may be data from an individual one of the sensors. For example, in the case of the EEG sensors 108, each channel may be measurements of voltage over time. If the signal is discretized such that there are measurements at discrete time points, a data set may be a matrix of N×m data points where N is the number of channels and m is the number of time points.

In the example embodiment of FIG. 1, the subject 102 may be undergoing a measurement protocol which is based on their reactions (or lack of reaction) to one or more stimuli. Accordingly, the room 104 may include a stimulus mechanism 116. The stimulus mechanism 116 may present some stimulus which may be detectable by one or more of the subject's 102 senses. For example the stimulus mechanism may be a speaker which emits various tones or a monitor which displays various images. The stimulus computer 114 may cause the stimulus mechanism 116 to provide one or more stimuluses. For example, the stimulus computer 114 may cause the stimulus mechanism to provide a sequence of stimuli at known times. The sensors 108 and 110 may record data before, during, and/or after the stimuli are provided.

The system electronics 120 may include various components for operating the various devices in the room 104 and/or recording data from the sensors 108 and 110. For example, the system electronics 120 may include EEG electronics 122 which may be coupled to the EEG sensors 108. The EEG electronics 122 may receive the raw signals from the EEG sensors 108 (e.g., voltage) and may combine the raw measurements into multi-channel data. In some embodiments, the EEG electronics 122 may perform one or more processing operations on the data from the EEG sensors 108. For example, the EEG electronics 122 may include a filter or a digitizer (e.g., an analog to digital converter). The MEG electronics 123 may be generally similar to the EEG electronics 122, except the MEG electronics 123 are coupled to the MEG sensors 110.

The system electronics 120 includes a peripheral interface unit 124 which may be used to control one or more aspects of the environment 100. For example, the peripheral interface unit 124 may include controls that may allow a user to indicate when a measurement sequence should begin. In another example the peripheral interface unit 124 may be used to operate various aspects of the room such as adjusting the support structure 106. The peripheral interface unit 124 may determine when measurement data should be captured from the EEG sensors 108 and/or MEG sensors 110.

In embodiments where the measurement involves stimulating the subject 102, the peripheral interface unit 124 may coordinate with the stimulus computer 114. For example, in an example measurement sequence, the peripheral interface unit 124 may capture data from the EEG and/or MEG sensors 108 and 110 as a 'before stimulation data set', may send a signal to the stimulus computer 114 to begin stimulation of the subject 102 and then capture data as a 'during stimulation data set', and may signal the stimulation computer 114 to stop stimulating the subject 102 and then may capture data as an 'after stimulation data set'.

In embodiments where the measurement sequence does not involve any stimulation (and wherein the stimulus computer 114 and the stimulus mechanism 116 may be omitted), the peripheral interface unit 124 may still control a timing of measurements. For example, a user may operate the peripheral interface unit 124 to indicate that the subject 102 is properly positioned for measurement and/or that extraneous personnel have exited the room 104.

The system electronics 120 may include signal processing electronics 126.

The signal processing electronics 126 may capture the signals from the EEG electronics 122 and/or MEG electronics 124, and may process those signals into a format which is acceptable to one or more computing devices (e.g., such as the acquisition workstation 128 and/or analysis workstation 130). For example, the signal processing electronics 126 may include an analog to digital converter (ADC) which may translate the signal measurements to digital signals. The signal processing electronics 126 may, in some embodiments, also include additional signal processing such as digital signal processing. For example, the signal processing electronics 126 may include one or more digital filters which be used to reduce noise in the recorded measurements.

The measurement protocol may be managed from an acquisition work station 128. The acquisition work station may include instructions for a particular measurement protocol. For example the acquisition work station 128 may control the stimulus computer 114, system electronics 120 and/or other components to collect measurements from the EEG sensors 108 and/or MEG sensors 110. In some embodiments, the acquisition work station 128 may include one or more user controls which may be used to adjust the measurement protocol. For example the acquisition work station 128 may include a number of saved measurement protocols, one of which may be selected. The selected measurement protocol may, in turn, have one or more adjustable parameters (e.g., timing of measurements, number of sensors, etc.). In some embodiments, the acquisition work station 128 may be a general purpose computer, which may execute acquisition software.

Data collected from the system electronics 120 may be provided to one or more analysis work station 130. The analysis work stations may process the recorded data in order to make it usable for one or more applications. For example, the analysis work station 130 may suppress artifacts in the recorded data in order to allow analysis of a particular signal of interest (e.g. a signal from the subject's 120 brain). In some embodiments, the analysis work station 130 may receive data from the sensors 108 and 110 as the data is being recorded (e.g., may be operating in a 'live' mode). In some embodiments, the analysis work station 130 may operate on measurements which were previously captured and stored. In some embodiments, the analysis work station 130 may be a general purpose computer which may execute analysis or data interpretation software.

After processing by the system electronics 120, the data collected from the EEG sensors 108 and/or MEG sensors 110 and used by the analysis work station 130 may take the form of a data matrix D, which is an N×m dimensional matrix, where N is the number of recording channels (e.g., the number of different individual sensors) and m is the number of discrete time points. It may be useful to consider the matrix of the data set D as containing a contribution from the signal of interest (e.g., a signal in the subject's 102 brain), a contribution from artifacts (e.g., electronic interference in the room 104, other brain signals which are not of interest), and a contribution from random noise. Accordingly, the data set D may be represented by Equation 1, below:

$$D = M_s X_s + M_a X_a + E \qquad \text{Eqn. 1}$$

In Equation 1, above, $M_s$ and $M_a$ are spatial bases spanning the spatial patterns of the signals of interest and artifacts, respectively. These bases have dimensions N×$n_s$ and N×$n_a$ respectively, where $n_s$ and $n_a$ represent the numbers of degrees of freedom of the signals and artifact signals respectively. For example, $n_s$ and $n_a$ may represent the detectable spatial complexity the signal of interest and the artifacts. The coefficient matrices $X_s$ and $X_a$ have dimensions of $n_s$×m and $n_a$×m, respectively, and may contain the time-dependent amplitude coefficients of the spatial basis components (e.g., $M_s$ and $M_a$, respectively). The noise matrix E is an N×m dimensional matrix which represents random, spatially uncorrelated noise.

Since the contribution from the signals of interest may generally be small compared to the contribution from noise and artifacts, it may be useful to extract the signals of interest (e.g., $M_s X_s$) from the data set D. Unfortunately, the signal subspaces spanning the signals of interest (e.g., $M_s$) and the artifacts (e.g., $M_a$) are generally not orthogonal from each other. Thus in general, knowing the signal subspace of the artifacts (e.g., $M_a$) may not be sufficient to separate the artifact contribution and signal contribution, since removing the artifact contribution from the data in this manner may also remove some (or all) of the signal contribution from the data as well.

As described in more detail herein, the analysis work station 130 may use a spatial model of the signal of interest to reduce (or eliminate) the contribution of artifacts from the data set D, while minimizing the impact this reduction has on the contribution from the signal of interest. The recorded data may be split by projecting the matrix based on the spatial model into projected data and residual data. The projected data set may contain contributions from the signal of interest and artifacts while the residual data set primarily contains the artifact and noise contribution (e.g., because the signal contribution was projected out). The residual data may be compared to the projected data or to the recorded data D, and artifacts may be removed from the projected data or the recorded data D. In this manner it may be possible to minimize the impact of the artifacts in the data set D based on a model of the signal. This may minimize (or eliminate) the need to make assumptions about and/or model the source of the artifact contributions.

The spatial model may generate an estimated spatial distribution of an electromagnetic field based on any feasible current (e.g., an arbitrary current) within a conductor (e.g., the brain). For example, a current of arbitrary location, direction, and/or magnitude may be used with the spatial model. In some embodiments, the arbitrary current may have properties based on an expected current which generates the signal of interest. For example the arbitrary current may have properties based on an expected location, direction, and/or magnitude of the current within the conductor. In some embodiments, the arbitrary current may have arbitrary properties that fall within a range of feasible properties for currents within the conductor. The spatial model may have different components to model different aspects of the electromagnetic field. For example, when the data set D includes measurements from MEG sensors 110, a magnetic field spatial model may be used to generate an estimated distribution of a magnetic field. When the data set D includes measurements from the EEG sensors 108, a voltage spatial model, which may be a particular form of an electric field spatial model, may be used to generate an estimated distribution of voltages.

In some embodiments, the spatial model may be used to determine a minimum number of channels N in the data set D. For example, the spatial model may have a number of degrees of freedom to the model. In order to ensure that the equations used to match the data set D and estimated distribution of the electromagnetic field given by the spatial model are overdetermined, it may be desirable to have a number of channels greater than the number of degrees of freedom of the model. For example the total number of sensors may be determined based on the degrees of freedom of the model. Since there may be separate magnetic and voltage spatial models, which may have different numbers of degrees of freedom, different numbers of MEG sensors 110 and EEG sensors 108 may be called for.

The example of FIG. 1 shows the components of the environment 100 placed in a certain relationship to the room 104, however it should be understood that other relationships may be used. For example, while FIG. 1 shows components such as the system electronics 120, acquisition work station 128 and analysis work station 130 outside of the room 104, in some embodiments one or more of these components may be positioned inside the room. Similarly, while the example environment of FIG. 1 shows the subject 102 inside of the room 104, in some embodiments, the room 104 may be a shielded chamber which encloses only part of the subject 102, a shielded partition, or may be omitted entirely.

Figure 2:
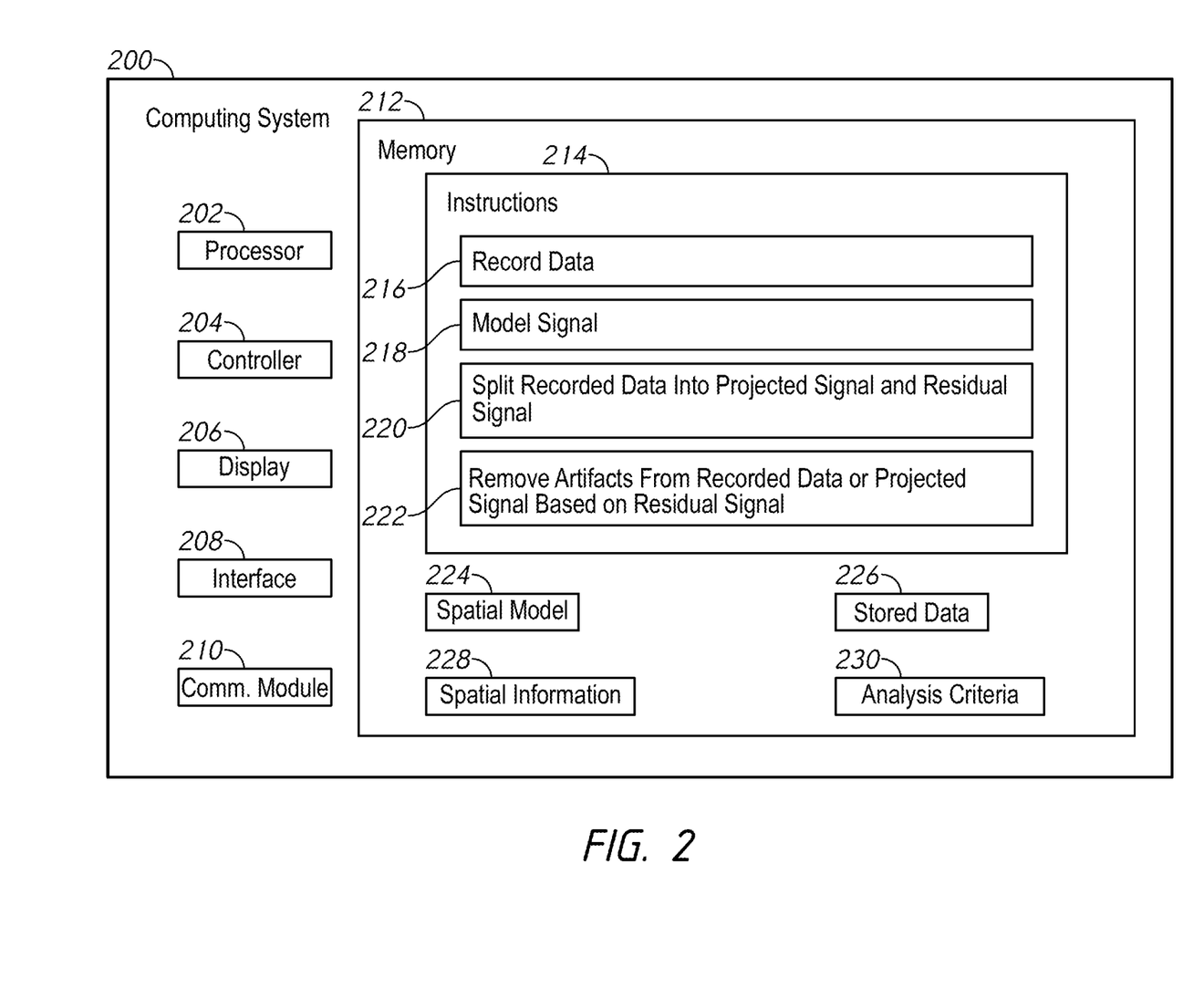
FIG. 2 is an analysis work station according to an embodiment of the present disclosure.

FIG. 2 is an analysis work station according to an embodiment of the present disclosure. The computing system 200 of FIG. 2 may, in some embodiments, be included in the analysis work station 130 of FIG. 1. The example computing system 200 of FIG. 2 is set up to execute instructions 214 which may be used to suppress artifacts in a data set D, which may be the data set D of Equation 1 captured by sensors such as the EEG sensors 108 and/or MEG sensors 110 of FIG. 1.

The computing system 200 includes a processor 202 which may execute one or more of the instructions 214 stored in the memory 212. The computing system 200 also includes a controller 204 which may be used to operate one or more components based on the instructions 214 executed by the processor 202.

The computing system 200 may include a display 206, such as a monitor, which may be used to present information to a user. The computing system 200 may include an interface 208, which may allow a user to interact with the computing system 200. For example, the interface 208 may be a mouse, keyboard, touchscreen, etc. The computing system 200 may also include a communications module, which may allow the computing system 200 to send and receive information. For example the communications module 210 may be a wired port such as a universal serial bus (USB) or may be a wireless (for example Bluetooth or WiFi).

The computing system 200 includes a memory (e.g., a hard drive, removable media such as a disc drive, etc.) which may be used to store information useful to the computing system 200. The memory 212 of the example computing system 200 of FIG. 2 is shown loaded with instructions 214 which may be used for suppression of artifacts in recorded data (D). The memory 212 is also shown as containing various data structures, pieces of information, and other instructions which may be useful for the suppression of artifacts in the measured data. For example, the memory 212 is shown as containing a spatial model 224, spatial information 228, which may be used as inputs to the spatial model 224, stored data 226, such as previously recorded measurements or data sets. The memory 212 may also include analysis criteria 230, which may be used to make various determinations about the data (either before or after the artifact suppression), for example, to make a diagnosis, classify a disease, monitor treatment, determine a course of treatment, etc., based on the recorded data.

The instructions 214 may include block 216, which describes recording data. In some embodiments, the recording step described in block 216 may be performed by an acquisition workstation (e.g., 128 of FIG. 1), which may be separate from the computing system 200. The recording of block 216 may generally describe a measurement protocol which may capture data from a subject using EEG and/or MEG sensors. The recorded data may take the form of a matrix D, which is an N×m dimensional matrix as described in Equation 1 above. In general, a data set D may include either EEG or MEG measurements. In some embodiments, both types of measurements may be recorded simultaneously, however they may be split into separate matrices D for the artifact suppression described herein. The instructions in block 216 may include saving the data into the stored data 226 (e.g., either locally or in a remote location such as the cloud) for later retrieval and subsequent analysis.

In some embodiments, the recording step described in block 216 may have been previously performed, and a data set D may be retrieved from the stored data 226. In some embodiments when a previously recorded data set is retrieved from the stored data 226, various information about the measurement protocol used to collect that data. In such an embodiment, the recording step of block 216 may be skipped, and the instructions may proceed with the retrieved data.

Block 218 describes modeling an expected signal based on a spatial model. In some embodiments, the modeling may occur prior to, simultaneous to, and/or after recording the data (or retrieving it from the stored data 226). The spatial model 224 may be used to model signal at each sensor produced by a signal of interest in the subject. For example, if an EEG is considered, the spatial model may be used to model the expected voltage at a given sensor location based on a current inside the subject's brain. In some embodiments, the spatial model 224 may include an electrical spatial model used to suppress artifacts in EEG signals, and a magnetic spatial model used to suppress artifacts in MEG signals. Example spatial models are described in more detail in FIG. 3.

Since the spatial model 224 may generate outputs which are function of location relative to a point of reference (e.g., a reference point in the subject's brain), the memory 212 may include spatial information 228. The spatial information 228 may include information about the placement of the sensors (e.g., EEG sensors 108 and/or MEG sensors 110) relative to the subject. In some embodiments, the spatial information 228 may be based on a standard placement of sensors about a subject. In some embodiments the spatial information 228 may include measured position information (e.g., from position sensors 112 of FIG. 1). In some embodiments, the spatial information 228 may also include information about likely sources of signals of interest within the subject. For example, if it is desired to monitor signals of interest from a particular anatomical region of the brain, the spatial information 228 may include information about the position of that region relative to the point of reference.

The modeled signal produced by the instructions of block 218 may be represented by a matrix $M_{s,e}$. The modeled signal matrix $M_{s,e}$ may generally be similar to the bases matrix $M_s$ of Equation 1, except that the modeled signal matrix represents data generated by the spatial model rather than recorded data.

In some embodiments, the instructions 214 may also include refining the model. For example, the model may be refined based on recorded data, which may be useful in case the recording channel are associated with calibration errors, rendering the estimated bases $M_{s,e}$ and $M_{a,e}$ inaccurate. The recorded data may have spatial data vectors which have a relatively small subspace with respect to $M_{s,e}$. The refinement basis (e.g., from the recorded data) may be merged with the computational basis (e.g., from the modeled data) to generate a refined model $M_{s,r}$. In some situations, the refined model $M_{s,r}$ may have increased accuracy compared to the unrefined model $M_{s,e}$. In embodiments where the refinement step is used, the refined model $M_{s,r}$ may be used in place of the model $M_{s,e}$ in subsequent steps.

The instructions 214 may continue with block 220, which describes splitting the recorded data (D) into a projected signal and a residual signal based on the spatial model ($M_{s,e}$ or $M_{s,r}$). The model $M_{s,e}$ may be used to project the signals from the recorded data along basis of the model $M_{s,r}$ (e.g., similar to the modeled brain signals). This may generate a projected data set which contains a mix of signal and artifact contributions and a residual data set which contains primarily artifact contributions.

For example, block 220 may involve forming a spatial parallel projection operator $P_\parallel$ corresponding to the model $M_{s,r}$ and forming an orthogonal projection operator $P_\perp$ corresponding to the model $M_{s,r}$, i.e., $P_\perp = I - P_\parallel$, where I is a N×N dimensional identity matrix. These operators may then be used by equations 2 and 3, below, to generate a projected data $D_\parallel$ and residual data $D_\perp$ respectively.

$$D_\parallel = P_\parallel D \qquad \text{Eqn. 2}$$

$$D_\perp = P_\perp D \qquad \text{Eqn. 3}$$

Block 220 may generally be followed by block 222, which describes removing or suppressing artifacts from the projected data (e.g., $D_\parallel$) based on the residual data ($D_\perp$). For example, since the residual data $D_\perp$ primarily contains contributions from artifacts, this may involve comparing the residual signal $D_\perp$ and the original data D or projected data $D_\parallel$, and removing contributions from the original signal D or projected signal $D_\parallel$ which are shared with the residual data $D_\perp$. For example, waveforms may be identified in the projected data $D_\parallel$ which may be primarily a mix of signal of interest waveforms and artifact waveforms, and waveforms may be identified in the residual data $D_\perp$ which may be primarily artifact waveforms. The waveforms may be compared and the artifact waveforms may be removed from the projected data $D_\parallel$ or from the original recorded data D. The identified artifact waveforms may be removed by an orthogonal projection operator (e.g., similar to Eqns. 2-3 above) in the time domain.

In some embodiments, block 222 may involve breaking down the projected and residual signals into basis components and projecting artifact elements out of the original recorded data D or the projected data $D_\parallel$. For example, block 222 may include decomposing the original recorded data D or projected data $D_\parallel$ and residual data $D_\perp$ into independent basis components in the spatial and temporal domains. In some embodiments, this may involve the singular value decomposition (SVD) method, which decomposes the signals in the forms of Equations 4 and 5, below:

$$D_\parallel = U_\parallel \Sigma_\parallel V_\parallel^T \qquad \text{Eqn. 4}$$

$$D_\perp = U_\perp \Sigma_\perp V_\perp^T \qquad \text{Eqn. 5}$$

where the U and V matrices contain the left and right singular vectors, respectively, and the diagonal $\Sigma$ matrices contain the corresponding singular values. Thus, the dimensions of the U, $\Sigma$, and V matrices are N×N, N×N, and m×N, respectively. In case a set of temporal components spanned by, e.g., a subset $V_{\perp,\tau} = [\vec{v}_1, \vec{v}_2, \ldots, \vec{v}_{n_\tau}]$ has been identified as artifact waveforms, then these artifacts can be removed from the data by an orthogonal projection in the temporal domain as Equation 6, below:

$$D_{\perp_\tau} = [I - V_{\perp,\tau} V_{\perp,\tau}^T) D^T]^T \qquad \text{Eqn. 6}$$

In some embodiments, other methods of decomposing the signals, such as principal component analysis (PCA) or independent component analysis (ICA) may be used. In embodiments where SVD is used, block 222 may also include examining the right-singular vectors (e.g., the temporal basis components) of $V_\perp$ in order of significance. Block 222 may also include labeling components as artifacts if they appear in the SVD of the residual data $D_\parallel$ at a higher order of significance than in the SVD of the projected data DN.

Once artifact waveforms are identified (e.g., either through SVD or some other method), the identified artifact waveforms may be removed from the original recorded data D or projected data $D_\parallel$ to generate processed data D'. For example, the identified artifact waveforms may be projected out of the projected data $D_\parallel$ and the residual may be the processed data D'. In some embodiments this may be generally similar to the projection operation described in block 220, except that the bases used for the projection may be based on the identified artifact waveforms rather than on the spatial model.

Once the artifacts in the recorded data D have been suppressed, the processed data D' may be used for one or more applications. For example, the processed data D' may be presented for review (e.g., by a clinician) on the display 206. In some embodiments, the processed data D' may be used by the analysis criteria 230. For example, the analysis criteria may include one or more criteria for tracking a disease. The analysis criteria 230 may be used to make a diagnosis based on the processed data, and/or may be used to monitor treatment/progression of a condition in the subject.

For example, if the subject (e.g., subject 102 of FIG. 1) is an epileptic, the processed data may be examined for "spikes" in the brain signal. This may involve inspection by a clinician or an automated analysis by the analysis criteria 230 (e.g., a threshold analysis). Based on the frequency and/or magnitude of the spikes, the subject may be monitored, the type of epilepsy may be diagnosed, a course of treatment may be determined or monitored, etc.

In some embodiments, the analysis criteria 230 may be used along with information about stimulus applied to the subject (e.g., by the stimulus mechanism 116). The analysis criteria 230 may match periods in the data to periods when the stimulus was being applied. Such information may be used for automatic analysis and/or the data may be annotated (e.g., with indications of when the stimulus was and was not applied) for presentation on the display 206.

Figure 3:
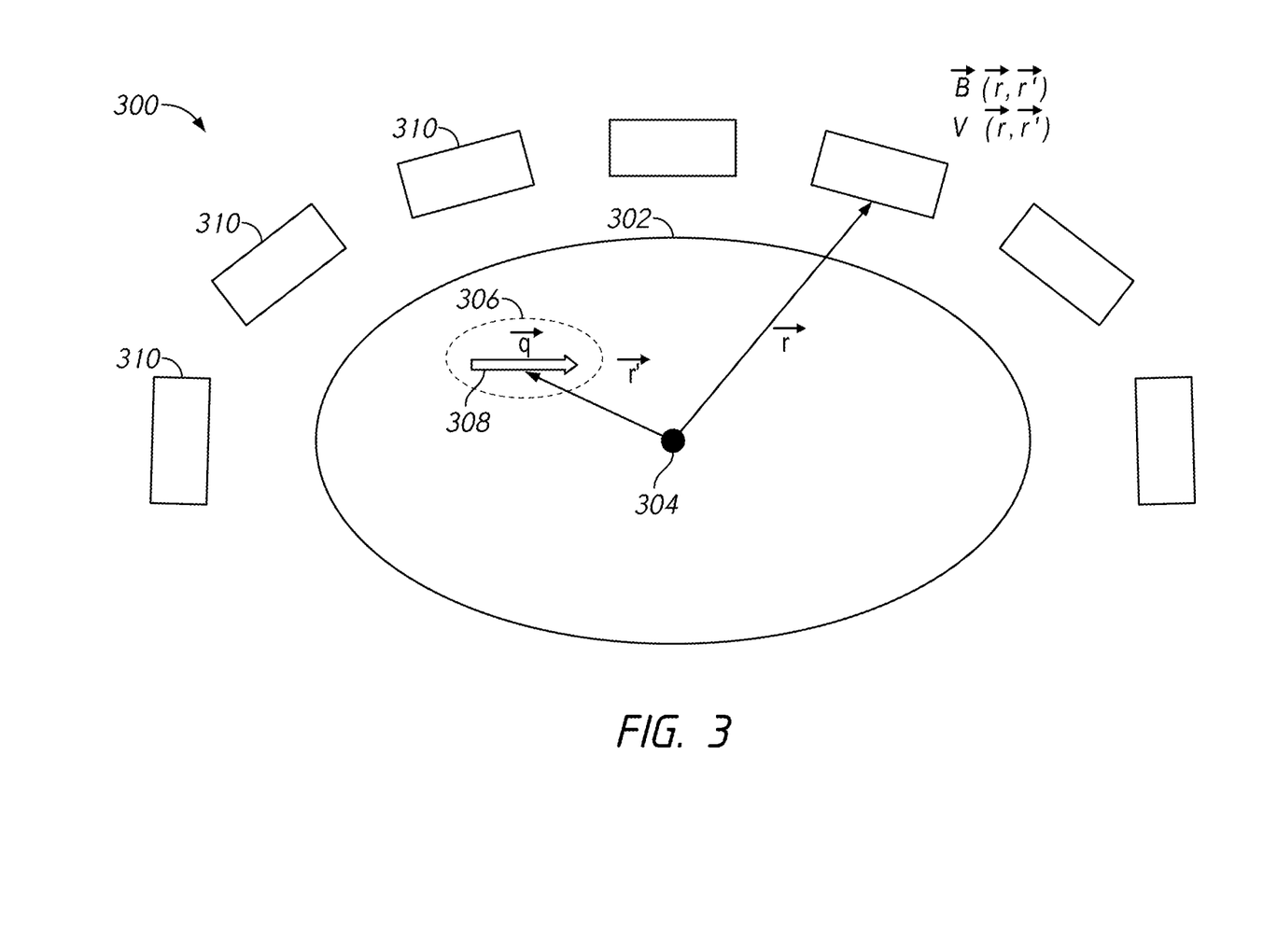
FIG. 3 is a block diagram of a spatial model according to an embodiment of the present disclosure.

FIG. 3 is a block diagram of a spatial model according to an embodiment of the present disclosure. The spatial model 300 may be used to estimate the contribution from a signal of interest (e.g., current 308) at the location of one or more sensors 310. The spatial model may be used as the spatial model 224 of FIG. 2 in some embodiments.

The spatial model 300 shows an example conductor, which in this case is a brain 302. The brain 302 includes an active region 306, which includes a current 308. The current 308 is represented by a vector $\vec{q}$. Laws of physics require that currents form closed loops, and $\vec{q}$ just represents an element of a current distribution. The brain 302 is surrounded by sensors 310, which may be positioned outside of the brain 302 (e.g., on or about the head). A reference point 304 may be defined within the brain 302 and used as the basis of a coordinate system. The spatial relationship between the current 308 and the reference point 304 may be given by the vector $\vec{r}'$. The spatial relationship between a given one of the sensors 310 and the reference point 304 may be given by the vector $\vec{r}$. The sensor 310 may experience a magnetic field $\vec{B}$ and a voltage V (which may be based on an electric field $\vec{E}$) due to the current $\vec{q}$. Both the magnetic field $\vec{B}$ and the voltage V may be functions of the spatial position vectors $\vec{r}$ and $\vec{r}'$. The magnetic field 9 may model the data which is recorded by MEG sensors (e.g., the MEG sensors 110 of FIG. 1) while the voltage V may model the signal recorded by EEG sensors (e.g., EEG sensors 108 of FIG. 1).

Modeling of the magnetic field $\vec{B}$ and voltage V may take advantage of the fact that the sensors 310 may generally be further away from the reference point 304 than the current 308. This may be due to the fact that the current 308 is within the brain 302, while the sensors 310 are positioned outside of the subject's head. In mathematical terms, in some embodiments the models may assume the relationship of Equation 7, below:

$$\|\vec{r}\| > \|\vec{r}'\| \qquad \text{Eqn. 7}$$

The magnetic field $\vec{B}$ may be modeled by Equation 8, below:

$$\vec{B}(\vec{r}, \vec{r}', \vec{q}) = \sum_{l,m}^{\infty} \alpha_{l,m}(\vec{r}', \vec{q}) \frac{\vec{\gamma}_{l,m}(\vec{r})}{r^{l+2}} \qquad \text{Eqn. 8}$$

where $\alpha_{l,m}(\vec{r}', \vec{q})$ is the magnetostatic multipole moment due to current q at location $\vec{r}'$, $\vec{\gamma}_{l,m}(\vec{r})$ is a vector spherical harmonic function, l is the order of the model, and m is the number of discrete time points in the measurement data D. Due to the principle of superposition, the total magnetic field due to all possible currents in the brain may be represented by Equation 9, below:

$$\vec{B}(\vec{r}) = \sum_{l,m}^{\infty} \alpha_{l,m} \frac{\vec{\gamma}_{l,m}(\vec{r})}{r^{l+2}} \qquad \text{Eqn. 9}$$

where the magnetostatic multipole moment $\alpha_{l,m}$ is a linear superposition of all $\alpha_{l,m}(\vec{r}', \vec{q})$ contributions.

The model of Equation 3 may be based on a quasistatic approximation of Maxwell's equations. The model of Equation 3 may have a number of degrees of freedom based on the order l. If l increases up to a maximum value of L (e.g., l=1, 2, . . . , L), then the number of degrees of freedom for the magnetic field model (nB) of Eqn. 8 (and/or Eqn. 9) may be given by Equation 10, below:

$$n_B(L) = (L+1)^2 - 1 \qquad \text{Eqn. 10}$$

As previously discussed, it may be useful for the number of degrees of freedom of the model to be smaller than the number of measurement channels (N) in the data matrix. For example, in a situation where L is 8, the number of degrees of freedom of the model may be 80 (e.g., as calculated by Eqn. 10, above). Accordingly, when recording MEG data, at least 81 different channels of data (e.g., 81 individual MEG sensors) may be used to collect data.

Modeling of the voltage V at a given position may be based on an electric field spatial model. Since voltage is a scalar based on the electric field vector at a point in space, the electric field spatial model may be simplified into a voltage model, such as the voltage model of equation 11, below:

$$V(\vec{r}, \vec{r}', \vec{q}) = \sum_{l,m}^{\infty} \delta_{l,m}(\vec{r}', \vec{q}) \frac{\omega_{l,m}(\vec{r})}{r^{l+2}} \qquad \text{Eqn. 11}$$

where $\delta_{l,m}(\vec{r}', \vec{q})$ is the electrostatic multipole moment due to current $\vec{q}$ at location $\vec{r}'$, to $_{l,m}(\vec{r})$ is a scalar spatial harmonic function, l is the order of the equation, and m is the number of discrete time points in the data matrix D. Due to the principle of superposition, the total electric voltage due to all possible currents in the brain may be represented by Equation 12, below:

$$V(\vec{r}) = \sum_{l,m}^{\infty} \delta_{l,m} \frac{\vec{\gamma}_{l,m}(\vec{r})}{r^{l+1}} \qquad \text{Eqn. 12}$$

where the electrostatic multipole moment $\delta_{l,m}$ is a linear e of all $\delta_{l,m}(\vec{r}', \vec{q})$ contributions. The voltage model of Equation 11 (and/or Eqn. 12) may be based on a solution to Laplace's equation. The number of degrees of freedom of the voltage model ($n_E$) for 1 up to a maximum value of L may be given by Equation 13, below:

$$n_E = (L+1)^2 \qquad \text{Eqn. 13}$$

In some embodiments, a relatively low order may be required to adequately model the voltage using Equations 11 or 12. This may be useful for reducing the number of sensor channels which are used. For example, if L is 2, then the number of degrees of freedom of the voltage model $n_E$ may be 9 (e.g., as calculated with Eqn. 13). Accordingly, at least 10 channels of EEG data (e.g., at least 10 EEG sensors) may be needed.

The magnetic field spatial model of Eqn. 8 (and/or Eqn. 9) and/or the voltage spatial model of Eqn. 11 (and/or Eqn. 12) may be used to generate the modeled signal matrix $M_{s,e}$, which in turn may be used separate the recorded data matrix D into projected data and residual data as described in regards to FIG. 2. The modeled signal matrix $M_{s,e}$ may generally be similar to the signal basis matrix $M_s$ of Eqn. 1. Accordingly, the spatial model (e.g., either magnetic or voltage) may generate a matrix of different values which may be split into a time dependent matrix $X_{s,e}$ and a spatial basis matrix $M_{s,e}$ in a manner generally similar to the way that the recorded data D is split into matrices $X_s$ and $M_s$ in Eqn. 1. However, the modeled data only has signal components, and thus the artifact and noise terms (e.g., $M_a X_a$ and E) do not need to be considered.

Figure 4A:
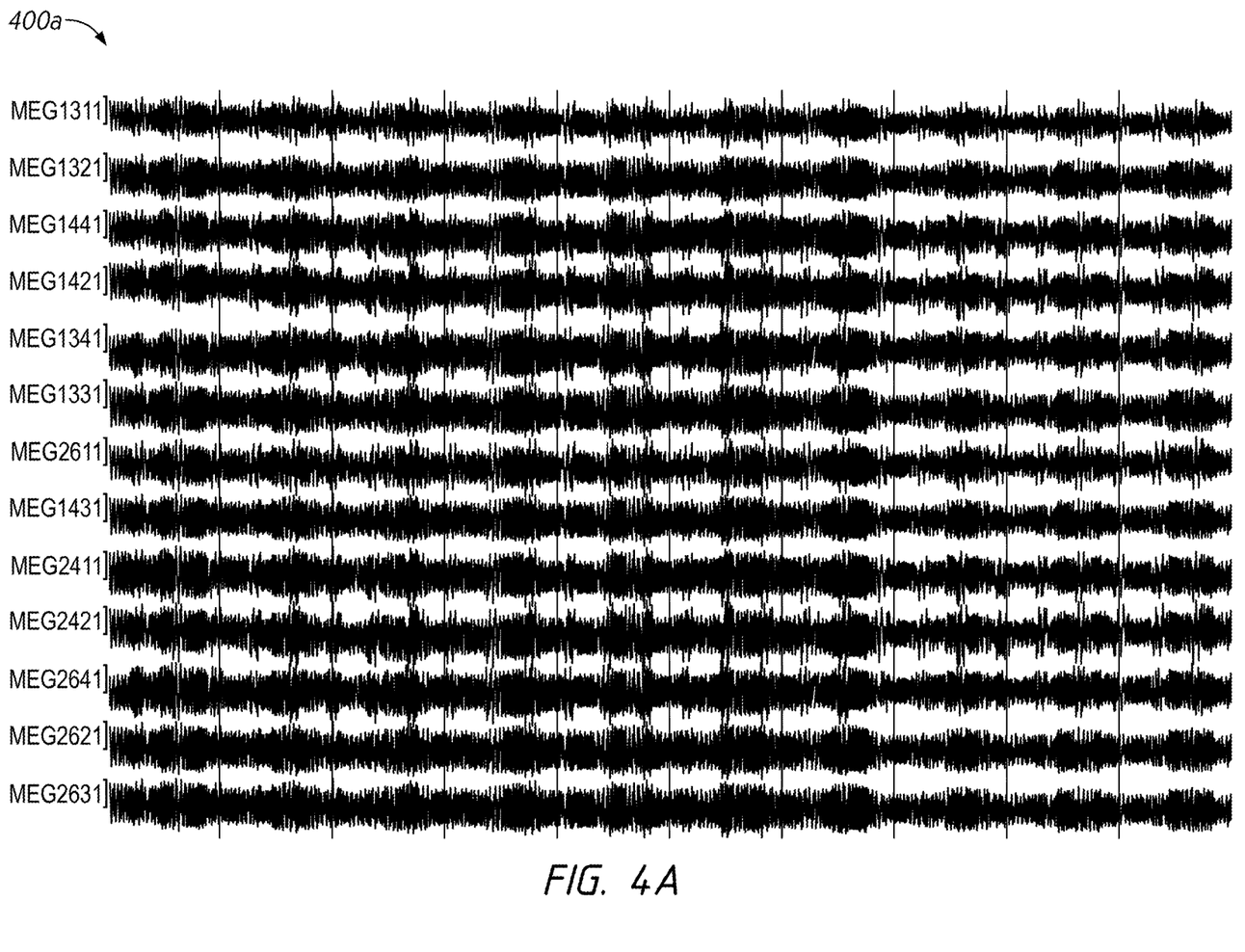
FIGS. 4A-4B are graphs depicting example MEG data before and after artifact suppression, respectively, according to an embodiment of the present disclosure.
Figure 4B:
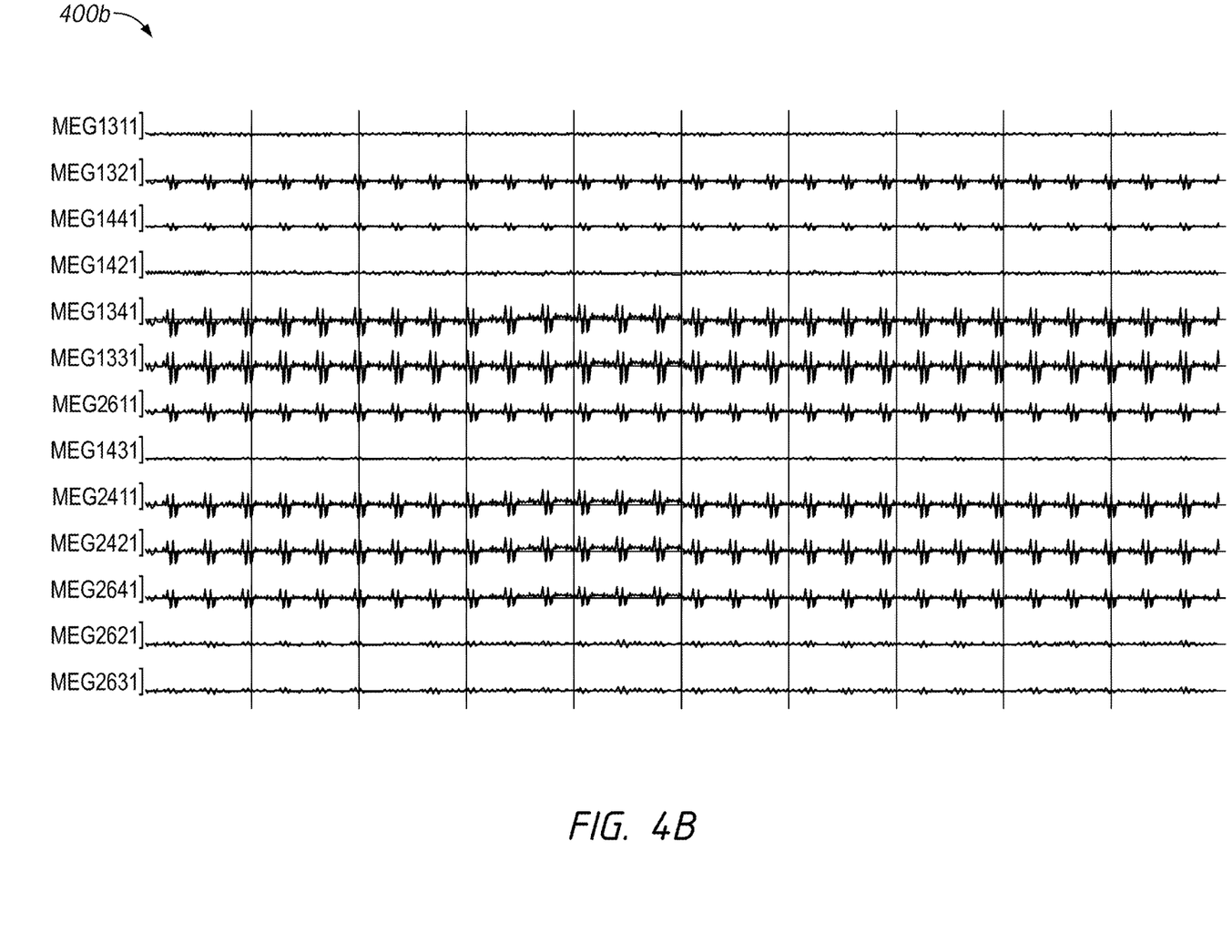

FIGS. 4A-4B are graphs depicting example MEG data before and after artifact suppression, respectively, according to an embodiment of the present disclosure. The graph 400a shows an example of MEG data before the artifacts are suppressed, while the graph 400b shows an example of processed MEG data after the artifacts are suppressed (e.g., using the instructions 214 of FIG. 2 and a magnetic field spatial model such as the one described in Eqn. 8) (and/or Eqn. 9). Both the graphs 400a and 400b show a number of different channels. Each channel shows signal amplitude along the vertical axis and time along the horizontal axis in a 10 second window of the data. As may be seen by comparing graphs 400a and 400b, the repeating signals of interest are much more apparent in the processed data shown in graph 400b. While a certain number of channels of data are shown in FIGS. 4A-4B, more or fewer channels may be used in other example embodiments.

Figure 5A:
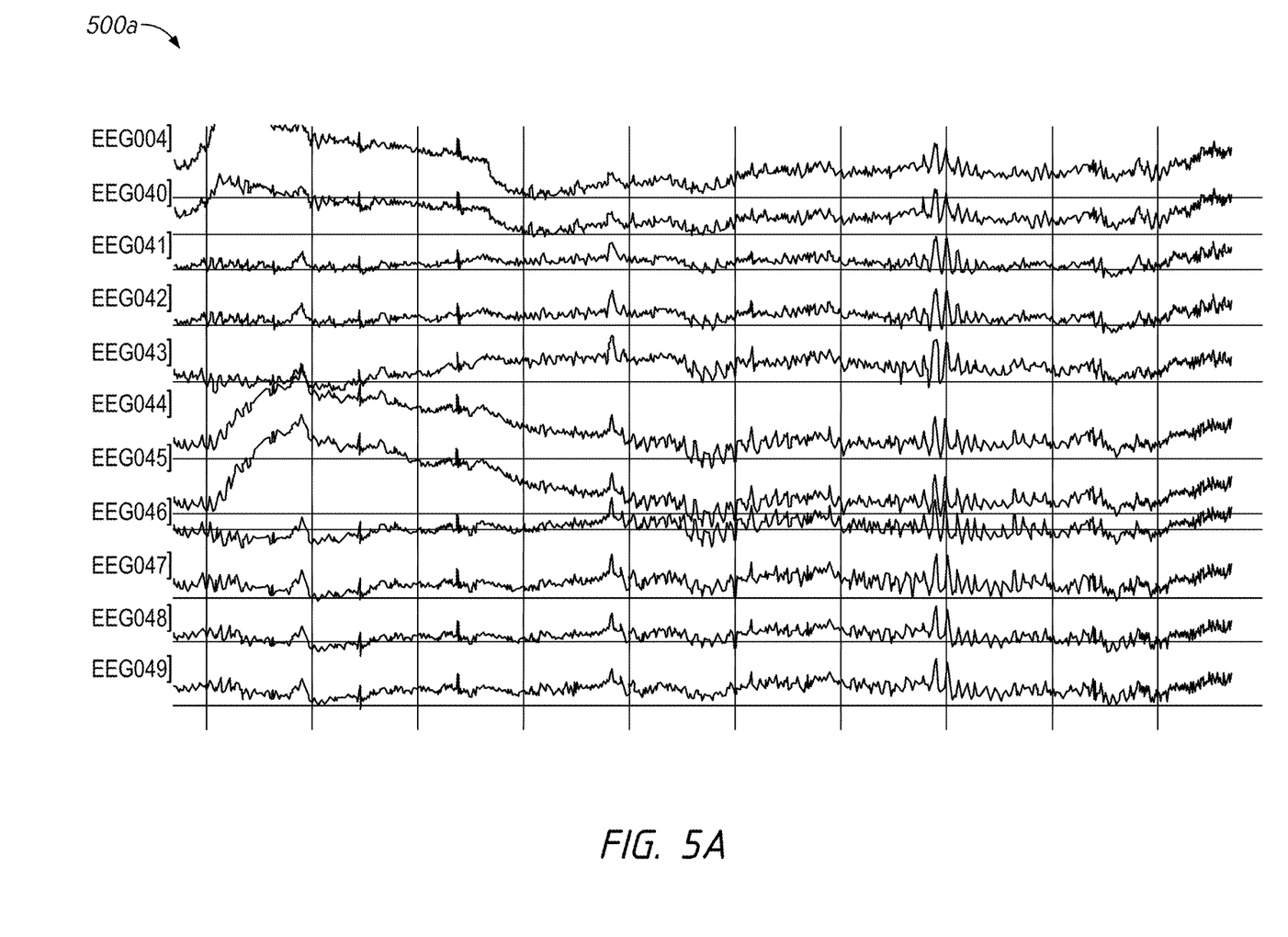
FIG. 5A-5B are graphs depicting example EEG data before and after artifact suppression, respectively, according to an embodiment of the present disclosure.
Figure 5B:
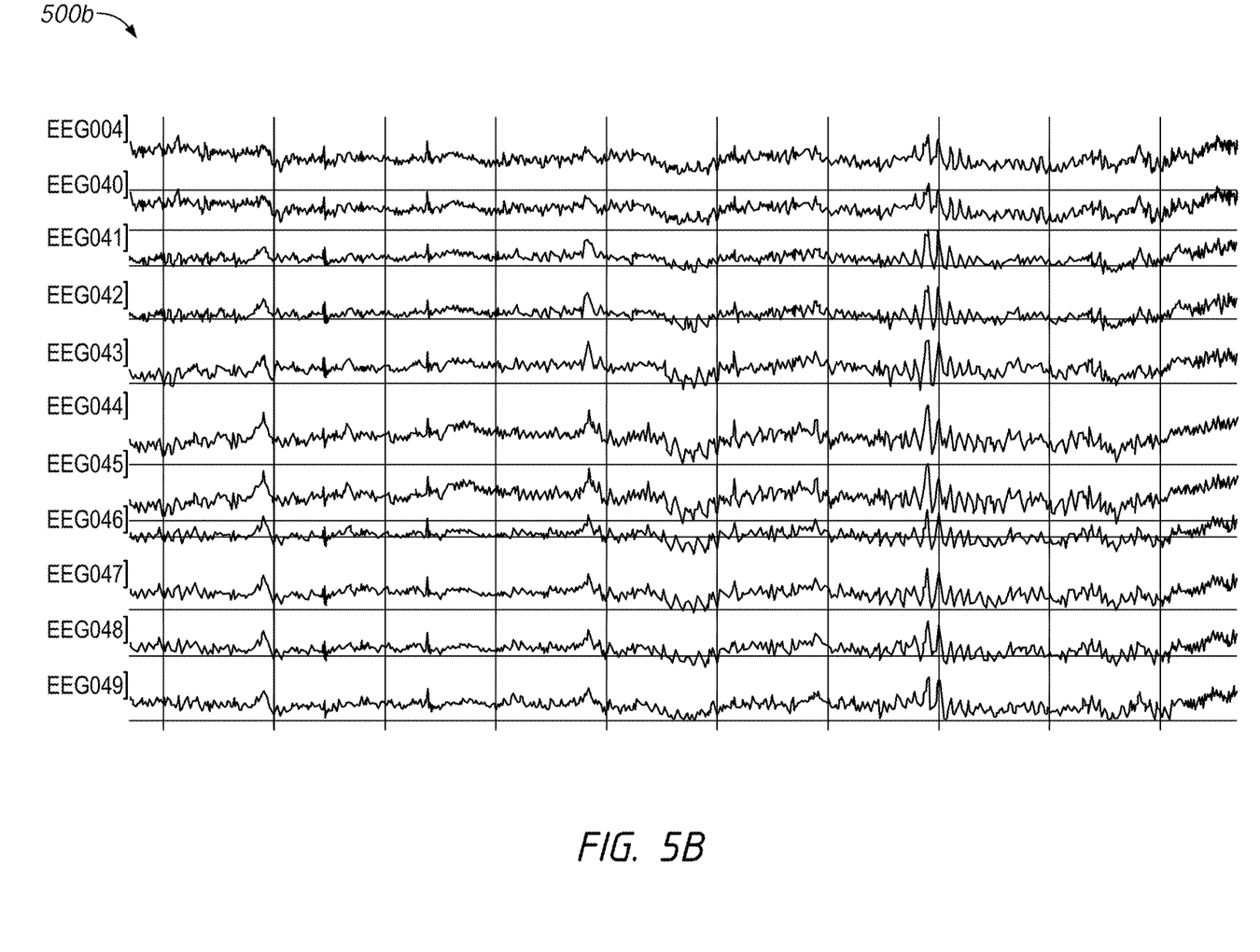

FIG. 5A-5B are graphs depicting example EEG data before and after artifact suppression, respectively, according to an embodiment of the present disclosure. The graph 500a shows an example of EEG data before the artifacts are suppressed, while the graph 500b shows an example of processed EEG data after the artifacts are suppressed (e.g., using the instructions 214 of FIG. 2 and an electrical field/voltage spatial model such as the one described in Eqn. 11 and/or Eqn. 12). Both the graphs 500a and 500b show a number of different channels. Each channel shows signal amplitude along the vertical axis and time along the horizontal axis in a 10 second window of the data. As may be seen by comparing graphs 500a and 500b, the processed data shown in graph 500b better highlights potential signals of interest by removing extraneous changes in the signal and increasing the relative contribution of certain waveforms compared to the data shown in the graphs 500a. While a certain number of channels of data are shown in FIGS. 5A-5B, more or fewer channels may be used in other example embodiments.

While the present disclosure is generally described with respect to EEG and MEG and monitoring of activity in the brain, it should be understood that similar techniques may be used to suppress artifacts from other types of electromagnetic recordings. For example, electromagnetic recordings may be made of neural activity in other parts of the body and/or of other types of organs with electromagnetic activity, such as muscle groups. Further, the techniques of the present disclosure may also be adapted for use in non-human subjects such as in veterinary medicine. Similarly, artifacts may also be suppressed using techniques similar to those of the present disclosure in electromagnetic recordings of non-biological phenomena such as in the research of the geomagnetic activity of the earth. In order to adapt the techniques described herein for other sources of electromagnetic signals, the spatial model may be adjusted to match parameters of source and sensors used to record signals from that source.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A method comprising:
   positioning a plurality of sensors outside a conductor, wherein a current inside the conductor generates an electromagnetic field;
   measuring a data set including a plurality of channels each measured by one of the plurality of sensors based on the electromagnetic field at the position of the sensor;
   generating an estimated distribution of the electromagnetic field at the positions of the plurality of sensors based on a spatial model of the electromagnetic field;
   separating the measured data set into a projected data set and a residual data set based on the estimated distribution of the electromagnetic field; and
   generating a processed data set by removing artifacts from the data set or the projected data set based on a comparison of the data set or the projected data set and the residual data set to identify artifact waveforms matched between the data set or the projected data set and the residual data set.

2. The method of claim 1, further comprising:
   decomposing the data set into a plurality of waveforms including signal of interest waveforms and artifact waveforms;
   decomposing the residual data set into a plurality of waveforms including artifact waveforms; and
   comparing the plurality of waveforms from the data set to the plurality of waveforms of the residual data and removing the artifacts based on the comparison.

3. The method of claim 2, wherein removing the artifacts comprises projecting the original recorded or projected data set based on the residual data set in the spatial or temporal domain.

4. The method of claim 1, further comprising:
   decomposing the projected data set into a plurality of waveforms including signal of interest waveforms and artifact waveforms;
   decomposing the residual data set into a plurality of waveforms including artifact waveforms; and
   comparing the plurality of waveforms from the projected data to the plurality of waveforms of the residual data and removing the artifacts based on the comparison.

5. The method of claim 1, wherein the conductor is a brain and wherein the plurality of sensors are configured to perform an electroencephalography (EEG) measurement or a magnetoencephalography (MEG) measurement.

6. The method of claim 1, further comprising:
   measuring position data with a position sensor; and
   determining the positions of the plurality of sensors based on the position data.

7. The method of claim 1, further comprising determining a number of the plurality of sensors based on a number of degrees of freedom of the spatial model, wherein the number of the plurality of sensors is greater than the number of degrees of freedom.

8. The method of claim 1, wherein generating the estimated distribution of the electromagnetic field comprises generating the spatial model of the electromagnetic field based on an arbitrary current within the conductor.

9. A system comprising:
a plurality of sensors positionable about a conductor, wherein the plurality of sensors is configured to produce a data set based on measurements of a signal of interest generated by a current within the conductor, wherein the data set includes contributions from the signal of interest and contributions from artifacts;
at least one processor; and
at least one memory, the at least one memory encoded with executable instructions, which, when executed by the at least one processor, cause the system to:
produce an estimated signal of interest based on a spatial model of the signal of interest and the positions of the plurality of sensors;
split the data set into projected data and residual data based on the estimated signal of interest;
compare the data set or the projected data and the residual data; and
generate processed data by reducing the contribution of artifacts in the data set or the projected data based on the comparison.

10. The system of claim 9, wherein the conductor is a brain and wherein the system is configured to collect electroencephalography (EEG) measurements or magnetoencephalography (MEG) measurements.

11. The system of claim 9, further comprising a stimulus mechanism configured to provide a stimulus to a subject and wherein the executable instructions further comprise instructions to cause the system to record the data set before the stimulus is provided, after the stimulus is provided, while the stimulus is provided, or combinations thereof.

12. The system of claim 9, wherein the executable instructions further comprise instructions to cause the system to:
decompose the projected data into projected waveforms;
decompose the residual data into residual waveforms;
match the projected waveforms and the residual waveforms; and
remove the matched waveforms from the projected waveforms to generate the processed data.

13. The system of claim 9, wherein the executable instructions further comprise instructions to cause the system to:
decompose the data set into data set waveforms;
decompose the residual data into residual waveforms;
match the data set waveforms and the residual waveforms; and
remove the matched waveforms from the data set waveforms to generate the processed data.

14. The system of claim 9, further comprising position sensors configured to determine the positions of the plurality of sensors.

15. The system of claim 9, wherein the system is an electroencephalography (EEG) system and wherein the executable instructions further comprise instructions to cause the system to:
estimate a voltage at each of the positions of the plurality of sensors based on a voltage spatial model.

16. A method comprising: positioning a plurality of sensors outside a conductor, wherein each of the plurality of sensors is configured to record a voltage based on an electromagnetic field generated by a current inside the conductor; measuring a data set based on the recorded voltages; determining a plurality of positions each associated with a position of one of the plurality of sensors; determining an estimated voltage at each of the plurality of positions based on a voltage spatial model of the electromagnetic field; and suppressing artifacts in the data set based on the estimated voltages; wherein suppressing the artifacts in the recorded voltages comprises: splitting the data set into a projected data set and a residual data set by projecting the data set based on the estimated voltages; matching waveforms in the data set or the projected data set to waveforms in the residual data set; and removing matched waveforms from the data set or the projected data set.

17. The method of claim 16, further comprising refining the spatial model based on a previously recorded data set.

18. The method of claim 16, wherein determining the estimated voltage is based on the plurality of positions about the conductor and an estimated location of the current within the conductor.

19. The method of claim 16, wherein the conductor is a brain of a subject, and wherein the method further comprises, based on the data set after suppressing the artifacts, monitoring the subject, diagnosing the subject, determining a treatment plan for the subject, classifying a condition of the subject, or combinations thereof.

20. The method of claim 16, wherein conductor is a brain of a subject and wherein the current is generated inside the brain due to biological activity of the brain of the subject.

* * * * *